United States Patent
Miller et al.

(10) Patent No.: US 10,154,862 B2
(45) Date of Patent: **\*Dec. 18, 2018**

(54) SYSTEM AND METHOD FOR PERFORMING VERTEBRAL REDUCTION USING A SLEEVE

(71) Applicant: Zimmer Spine, Inc., Edina, MN (US)

(72) Inventors: Peter Thomas Miller, Austin, TX (US); Charles R. Forton, Austin, TX (US); Bruce A. Riceman, Leander, TX (US); Larry T. Khoo, Studio City, CA (US); Reginald J. Davis, Cockeysville, MD (US); Michael Scott Hisey, Flower Mound, TX (US)

(73) Assignee: Zimmer Spine, Inc., Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,499

(22) Filed: Jun. 9, 2017

(65) Prior Publication Data
US 2017/0273725 A1    Sep. 28, 2017

Related U.S. Application Data

(63) Continuation of application No. 12/539,468, filed on Aug. 11, 2009, now Pat. No. 9,707,019.

(51) Int. Cl.
*A61B 17/70* (2006.01)

(52) U.S. Cl.
CPC ................ *A61B 17/7091* (2013.01)

(58) Field of Classification Search
CPC ............ A61B 17/7083; A61B 17/7085; A61B 17/7091; A61B 17/7086
See application file for complete search history.

(56) References Cited

U.S. PATENT DOCUMENTS

| | | | |
|---|---|---|---|
| 5,586,984 A | 12/1996 | Errico et al. | |
| 6,648,888 B1 | 11/2003 | Shluzas | |
| 7,160,300 B2 | 1/2007 | Jackson | |
| 7,179,261 B2 | 2/2007 | Sicvol et al. | |
| 7,278,995 B2 | 10/2007 | Nichols et al. | |

(Continued)

FOREIGN PATENT DOCUMENTS

| | | |
|---|---|---|
| EP | 2283787 B1 | 9/2012 |
| EP | 2522287 | 11/2012 |

OTHER PUBLICATIONS

"U.S. Appl. No. 12/539,468, Response filed Oct. 28, 2016 to Non Final Office Action dated Jul. 29, 2016", 13 pgs.

(Continued)

*Primary Examiner* — Jan Christopher Merene
*Assistant Examiner* — Atiya Mahmud
(74) *Attorney, Agent, or Firm* — Schwegman Lundberg & Woessner, P.A.

(57) ABSTRACT

Embodiments described herein provide systems and methods for vertebral reduction using sleeves detachably coupled to collars of bone fasteners. The reduction can be performed during a minimally invasive procedure for implanting spinal stabilization systems. A sleeve can include internal threads that match threads on the respective collar to form a continuous set of threads. Threads on a closure member can be engaged with the threads on the sleeve and the closure member turned to translate the closure member along the sleeve. The closure member can be used to push a rod relative to the collar to which the sleeve is attached to cause a vertebral body to move.

14 Claims, 7 Drawing Sheets

(56) References Cited

U.S. PATENT DOCUMENTS

| | | | |
|---|---|---|---|
| 7,491,218 | B2 | 2/2009 | Landry et al. |
| 7,520,879 | B2 | 4/2009 | Justis et al. |
| 7,591,836 | B2 | 9/2009 | Dick et al. |
| 9,707,019 | B2 | 7/2017 | Miller et al. |
| 2004/0215190 | A1 | 10/2004 | Nguyen et al. |
| 2004/0249378 | A1 | 12/2004 | Saint Martin et al. |
| 2005/0065517 | A1 | 3/2005 | Chin |
| 2005/0119667 | A1 | 6/2005 | Leport et al. |
| 2005/0131408 | A1 | 6/2005 | Sicvol et al. |
| 2005/0131421 | A1 | 6/2005 | Anderson et al. |
| 2005/0149053 | A1 | 7/2005 | Varieur et al. |
| 2005/0154389 | A1 | 7/2005 | Selover et al. |
| 2005/0182410 | A1 | 8/2005 | Jackson |
| 2005/0192570 | A1 | 9/2005 | Jackson |
| 2005/0192579 | A1 | 9/2005 | Jackson |
| 2005/0273101 | A1 | 12/2005 | Schumacher |
| 2006/0036244 | A1 | 2/2006 | Spitler et al. |
| 2006/0036252 | A1 | 2/2006 | Baynham et al. |
| 2006/0036254 | A1 | 2/2006 | Lim |
| 2006/0074418 | A1 | 4/2006 | Jackson |
| 2006/0111713 | A1 | 5/2006 | Jackson |
| 2006/0142761 | A1 | 6/2006 | Landry et al. |
| 2006/0184178 | A1 | 8/2006 | Jackson |
| 2007/0016194 | A1 | 1/2007 | Shaolian et al. |
| 2007/0073294 | A1 | 3/2007 | Chin et al. |
| 2007/0100352 | A1 | 5/2007 | Deffenbaugh et al. |
| 2007/0162010 | A1 | 7/2007 | Chao et al. |
| 2007/0179502 | A1 | 8/2007 | Raynor et al. |
| 2007/0191840 | A1 | 8/2007 | Pond et al. |
| 2007/0233079 | A1 | 10/2007 | Fallin et al. |
| 2007/0288026 | A1 | 12/2007 | Shluzas |
| 2008/0009862 | A1 | 1/2008 | Hoffman |
| 2008/0077139 | A1 | 3/2008 | Landry et al. |
| 2008/0082103 | A1 | 4/2008 | Hutton et al. |
| 2008/0091213 | A1 | 4/2008 | Jackson |
| 2008/0114403 | A1 | 5/2008 | Kuester et al. |
| 2008/0119849 | A1 | 5/2008 | Beardsley et al. |
| 2008/0132957 | A1 | 6/2008 | Matthis et al. |
| 2008/0300638 | A1 | 12/2008 | Beardsley et al. |
| 2009/0005814 | A1 | 1/2009 | Miller et al. |
| 2009/0099605 | A1 | 4/2009 | Fallin et al. |
| 2009/0234392 | A1 | 9/2009 | Dziedzic et al. |
| 2011/0040328 | A1 | 2/2011 | Miller et al. |

OTHER PUBLICATIONS

"U.S. Appl. No. 12/186,393, Non Final Office Action dated Aug. 15, 2011", 10 pgs.
"U.S. Appl. No. 12/539,468, Advisory Action dated Sep. 18, 2014", 3 pgs.
"U.S. Appl. No. 12/539,468, Examiner Interview Summary dated May 3, 2012", 3 pgs.
"U.S. Appl. No. 12/539,468, Final Office Action dated Jan. 4, 2016", 29 pgs.
"U.S. Appl. No. 12/539,468, Final Office Action dated Jun. 18, 2014", 30 pgs.
"U.S. Appl. No. 12/539,468, Final Office Action dated Oct. 3, 2012", 21 pgs.
"U.S. Appl. No. 12/539,468, Non Final Office Action dated Jan. 31, 2012", 15 pgs.
"U.S. Appl. No. 12/539,468, Non Final Office Action dated Jun. 17, 2015", 29 pgs.
"U.S. Appl. No. 12/539,468, Non Final Office Action dated Jun. 23, 2011", 14 pgs.
"U.S. Appl. No. 12/539,468, Non Final Office Action dated Jul. 29, 2016", 29 pgs.
"U.S. Appl. No. 12/539,468, Non Final Office Action dated Dec. 3, 2013", 29 pgs.
"U.S. Appl. No. 12/539,468, Notice of Allowance dated Mar. 10, 2017", 9 pgs.
"U.S. Appl. No. 12/539,468, Preliminary Amendment filed May 13, 2011", 9 pgs.
"U.S. Appl. No. 12/539,468, Response filed Mar. 3, 2014 to Non Final Office Action dated Dec. 3, 2013", 13 pgs.
"U.S. Appl. No. 12/539,468, Response filed Apr. 4, 2016 to Final Office Action dated Jan. 4, 2016", 14 pgs.
"U.S. Appl. No. 12/539,468, Response filed May 29, 2012 to Non Final Office Action dated Jan. 31, 2012", 11 pgs.
"U.S. Appl. No. 12/539,468, Response filed Aug. 15, 2014 to Final Office Action dated Jun. 18, 2014", 12 pgs.
"U.S. Appl. No. 12/539,468, Response filed Sep. 21, 2015 to Non-Final Office Action dated Jun. 17, 2015", 13 pgs.
"U.S. Appl. No. 12/539,468, Response filed Sep. 23, 2011 to Non Final Office Action dated Jun. 23, 2011", 14 pgs.
"U.S. Appl. No. 12/539,468, Response filed Oct. 15, 2014 to Advisory Action dated Sep. 18, 2014", 14 pgs.
"U.S. Appl. No. 12/539,468, Response filed Dec. 3, 2012 to Final Office Action dated Oct. 3, 2012", 11 pgs.
"European Application Serial No. 10008069.6, Decision to Grant dated Aug. 23, 2012", 2 pgs.
"European Application Serial No. 10008069.6, Examination Notification Art. 94(3) dated Sep. 12, 2011", 5 pgs.
"European Application Serial No. 10008069.6, Extended European Search Report dated Nov. 9, 2010", 7 pgs.
"European Application Serial No. 10008069.6, Office Action dated Feb. 21, 2011", 2 pgs.
"European Application Serial No. 10008069.6, Office Action dated Mar. 23, 2012", 7 pgs.
"European Application Serial No. 10008069.6, Response filed Jan. 18, 2012 to Examination Notification Art. 94(3) dated Sep. 12, 2011", 14 pgs.
"European Application Serial No. 10008069.6, Response filed Aug. 11, 2011 to Extended European Search Report dated Nov. 9, 2010", 14 pgs.
"European Application Serial No. 12180027.0, Examination Notification Art. 94(3) dated Jan. 30, 2015", 6 pgs.
"European Application Serial No. 12180027.0, Examination Notification Art. 94(3) dated Apr. 23, 2014", 6 pgs.
"European Application Serial No. 12180027.0, Examination Notification Art. 94(3) dated Jun. 17, 2013", 6 pgs.
"European Application Serial No. 12180027.0, Extended European Search Report dated Sep. 11, 2012", 7 pgs.
"European Application Serial No. 12180027.0, Office Action dated Jul. 7, 2015", 1 pg.
"European Application Serial No. 12180027.0, Office Action dated Nov. 19, 2012", 2 pgs.
"European Application Serial No. 12180027.0, Response filed May 14, 2013 to Extended European Search Report dated Sep. 11, 2012", 14 pgs.
"European Application Serial No. 12180027.0, Response filed Aug. 19, 2014 to Examination Notification Art. 94(3) dated Apr. 23, 2014", 3 pgs.

SYSTEM AND METHOD FOR PERFORMING VERTEBRAL REDUCTION USING A SLEEVE

TECHNICAL FIELD

This disclosure relates generally to spinal implants and more particularly to embodiments of a system using extender sleeve reduction

BACKGROUND

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

During a spinal stabilization procedure, a rod is attached to multiple vertebrae using bone screws. The rod provides stabilization for the vertebrae. During insertion of the rod, the offset between vertebrae may have to be lessened in a process called reduction. Typically during reduction, a tool is used to press down on a spinal stabilization rod while another tool is used to pull up on the collar of a bone screw (or sleeve attached to the collar) causing the rod and collar to move toward each other and, hence, the vertebra to which the collar is attached to move. The reducer tools often require additional space at the surgical site.

SUMMARY

This disclosure and various features and advantageous details thereof are explained more fully with reference to the exemplary, and therefore non-limiting, embodiments illustrated in the accompanying drawings and detailed in the following description. Descriptions of known starting materials and processes may be omitted so as not to unnecessarily obscure the disclosure in detail. It should be understood, however, that the detailed description and the specific examples, while indicating the preferred embodiments, are given by way of illustration only and not by way of limitation. Various substitutions, modifications, additions and/or rearrangements within the spirit and/or scope of the underlying inventive concept will become apparent to those skilled in the art from this disclosure.

Embodiments described herein provide systems and methods for using a sleeve to perform vertebral reduction procedures. One embodiment includes a reduction system, comprising a bone fastener assembly and a sleeve adapted for use in minimally invasive procedures. The bone fastener assembly can comprise collar having a first set of threads internal to the collar a slot sized to fit a spinal stabilization rod. The sleeve can comprise a body detachably coupled to the collar. The body of the sleeve can define at least one channel sized to allow a portion of the spinal stabilization rod to move along said channel and a passage extending from a first end of said sleeve to a second end of said sleeve sized to fit a closure member. The body can comprise a second set of threads internal to the passage matching the first set of threads on the collar and positioned to form a continuous set of threads with the first set threads. A closure member can be sized to fit the passage and comprise an external set of the threads complimentary to the first set of threads and the second set of thread. The closure member can be adapted to secure the spinal stabilization rod in the collar. The continuous set of threads can be continuous in the sense that a closure member can thread from the sleeve to the collar using the set of threads. The continuous set of threads may have gaps in the threads, such as where openings occur in the collar or sleeve or where the threads transition from the sleeve and the collar.

One embodiment of a method of performing a spinal reduction procedure can comprise providing a bone screw coupled to vertebrae, the bone screw and a sleeve. The bone screw can comprise a collar having a first set of threads internal to the collar and define a slot sized to fit a spinal stabilization rod. The sleeve can be detachably coupled to the collar. The sleeve can comprise a body having at least one channel sized to allow a portion of the spinal stabilization rod to move along said channel. The body can also define a passage extending from a first end of the sleeve to a second end of the sleeve. The passage can be sized to fit a closure member. The body can comprise a second set of threads internal to the passage matching the first set of threads on the collar and positioned to form a continuous set of threads with the first set threads. The method can further comprise inserting a portion of a spinal stabilization rod into the channel of the sleeve, inserting a closure member in the passage of the sleeve, fully engaging threads on the closure member with the second set of threads before the closure member contacts the spinal stabilization rod and turning the closure member with a tool to cause the closure member move the rod and collar relative to each other to cause the rod to seat in the collar and the vertebrae to which the bone screw is coupled to translate.

Another embodiment can comprise a spinal implantation system, comprising a spinal stabilization rod, a first bone fastener assembly, a second bone fastener assembly, a first quick connect sleeve, a second quick connect sleeve and a spinal stabilization rod. At least one of the quick connect sleeves can comprise a body defining a passage sized to fit a closure member from a first end of the sleeve to a second end of the sleeve, a channel sized to fit at least a portion of the spinal stabilization rod and at least one or more additional channels to fit a portion of a coupling member. The first sleeve can also include a coupling member having a head portion and a body portion. Additionally, the sleeve can include a set of threads disposed internal to the passage. The body portion of the coupling member can be at least partially disposed in the one or more additional channels and be adapted to engage with a collar portion of the first bone fastener assembly to prevent translation of the collar portion of the first bone fastener assembly relative to the first sleeve. The set of threads can be adapted to form a continuous set of threads on a collar portion of the first bone fastener assembly and engage complementary threads of a closure member. The second sleeve may also include threads for reduction or be a sleeve without internal threads for reduction.

BRIEF DESCRIPTION OF THE DRAWINGS

A more complete understanding of the embodiments and the advantages thereof may be acquired by referring to the following description, taken in conjunction with the accompanying drawings in which like reference numbers indicate like features and wherein.

DETAILED DESCRIPTION

Figure 1:
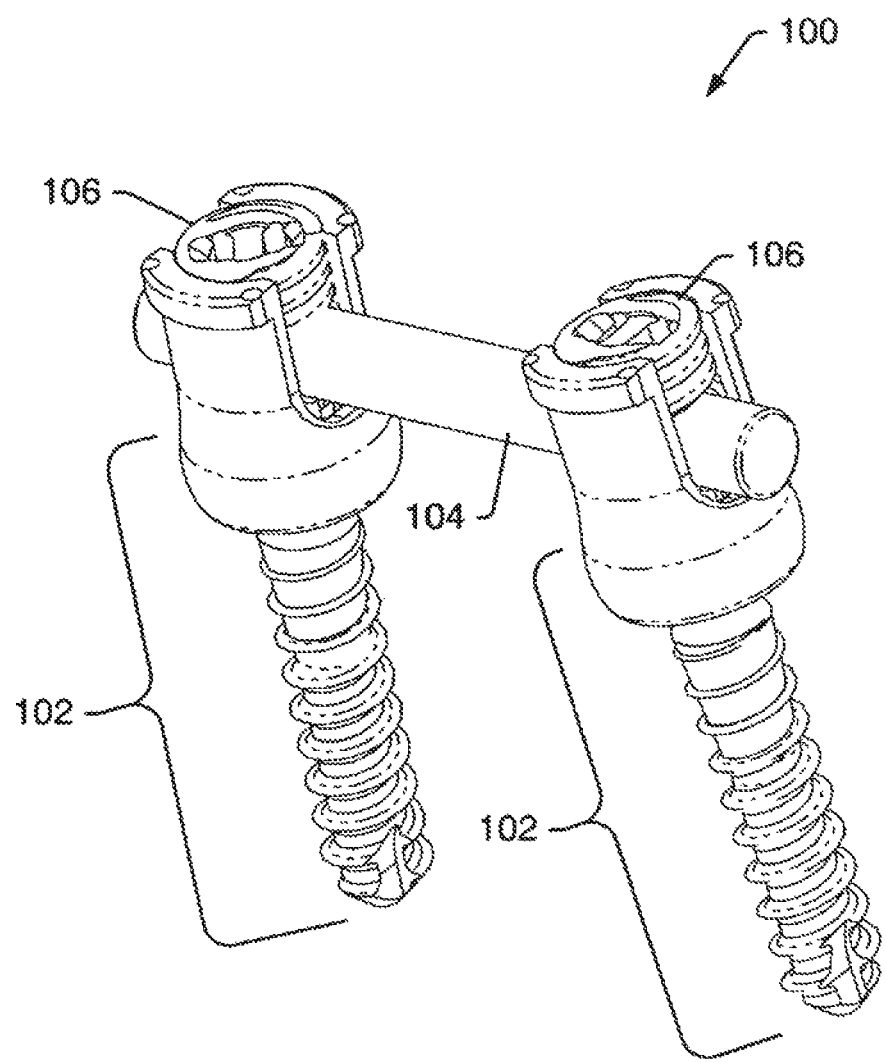
FIG. 1 depicts one example of spinal stabilization system 100 that may be implanted using a minimally invasive surgical procedure.

Different instruments may be used to form a spinal stabilization system in a patient. The instruments may include, but are not limited to, positioning needles, guide wires, sleeves, bone fastener driver, mallets, tissue wedges, tissue retractors, tissue dilators, bone awls, taps, and an rod length estimator. An instrumentation kit may provide instruments and spinal stabilization system components necessary for forming a spinal stabilization system in a patient. An exemplary instrumentation kit may include, but is not limited to, two or more detachable members (e.g., extender sleeves), a tissue wedge, a rod inserter, a counter torque wrench, an estimating tool, a seater, closure member driver, and/or combinations thereof. Examples of detachable members may include quick-connect sleeve assemblies that can allow for quick connection to a bone fastener (e.g., a lumbar fixation screw) during a spinal surgical procedure.

An exemplary method for inserting a stabilization system in a spine may involve determining one or more vertebrae of the spine to be targeted for stabilization, making an incision in the skin, inserting a spinal stabilization system utilizing quick-connect sleeve assemblies, and closing the incision in the skin.

During some surgical procedures, images of a patient may be taken to assist in determining target locations for insertion of bone fastener assemblies in vertebrae to be stabilized. A marking or markings may be made on the patient to indicate the target locations. An incision may be made in the patient's skin between the target locations. In some cases, the incision may be enlarged after insertion of a first bone fastener assembly. The targeting needle may be inserted into a first pedicle.

After insertion of the targeting needle, a guide wire may be inserted through a hollow shaft of the targeting needle into the first pedicle. The targeting needle may be removed from the patient. A first bone fastener assembly coupled to a first extender sleeve may be inserted into the first pedicle. A similar procedure can be followed to couple a bone fastener with extender sleeve to a second pedicle.

A rod (e.g., a rigid or dynamic stabilization rod) may be to the bone fasteners using a rod insertion tool that allows the rod to be inserted into the body in a first orientation with a reduced profile. When the rod is at desired position, the rod insertion tool can rotate the rod to span the bone fasteners. The rod may be seated in the collars of the bone fastener assemblies. A position of the rod in the collars may be confirmed using fluoroscopic imaging. After confirming the position of the rod, a first closure member coupled to a driver may be advanced down the first quick-connect sleeve assembly. The first closure member may be coupled to the first collar. A counter torque wrench may be coupled to the first quick-connect sleeve assembly. The driver may be removed from the first closure member after coupling the first closure member to the first collar. Similarly, the driver can be used to couple a second closure member to the second collar.

In some cases, the bone fastener assemblies may be offset relative to each other due to positioning of the vertebrae such that one of the vertebrae must be moved to allow the rod to seat in the first or second collar. Embodiments described herein provide systems and methods for using the closure member to perform reduction to reduce the offset between the vertebrae. This reduces the need for a separate reduction tool during minimally invasive surgical procedures.

In minimally invasive procedures, a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures and reduce recovery time for the patient as compared to invasive spinal procedures.

FIG. 1 depicts one example of spinal stabilization system 100 that may be implanted using a minimally invasive surgical procedure. Spinal stabilization system 100 may include bone fastener assemblies 102, stabilization rod 104, and/or closure members 106. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 102 are placed. In other embodiments, multi-level spinal stabilization systems may include additional bone fastener assemblies to couple to one or more other vertebrae.

Spinal stabilization system 100 can be inserted using sleeves that are designed for use in minimally invasive procedures. Such sleeves attach to the collar of a bone fastener assembly and provide a working passage to the collar. Various embodiments of sleeves for minimally invasive surgery are known in the art. Examples of sleeves are described in U.S. patent application Ser. No. 11/779,406 entitled "SPINAL STABILIZATION SYSTEMS WITH QUICK-CONNECT SLEEVE ASSEMBLIES FOR USE IN SURGICAL PROCEDURES" by Landry et al., which is a continuation-in-part application of U.S. patent application Ser. No. 10/697,793, entitled "SPINAL STABILIZATION SYSTEMS AND METHODS," filed Oct. 30, 2003, which claims priority to U.S. Provisional Patent Application No. 60/422,455, entitled "SPINAL STABILIZATION SYSTEM USING POLYAXIAL MEMBERS," filed Oct. 30, 2002; U.S. Provisional Patent Application No. 60/466,091, entitled "SPINAL STABILIZATION SYSTEMS AND METHODS USING MINIMALLY INVASIVE SURGICAL PROCEDURES," filed Apr. 28, 2003; and U.S. Provisional Patent Application No. 60/471,254, entitled "SPINAL STABILIZATION SYSTEMS AND METHODS USING MINIMALLY INVASIVE SURGICAL PROCEDURES," filed May 16, 2003. All of these patent applications are hereby fully incorporated by reference herein for all purposes.

A sleeve can attach to the collar of a bone fastener assembly and provide a passage for tools to access the bone fastener assembly. A distal end of a sleeve may be tapered or angled to reduce bulk at a surgical site. Instruments may be inserted into the detachable member to manipulate the bone fastener assembly. Movement of the sleeve may alter an orientation of a collar relative to a bone fastener of the bone fastener assembly. In some embodiments, a sleeve may be used as a reducer during a spinal stabilization procedure.

A sleeve for a single-level vertebral stabilization system may include one or more channels in a wall of the detachable member to allow access to an adjacent vertebra. For example, one or more single or multi-channel sleeves may be used. Channels may provide flexibility to or enhance flexibility of a multi-channel sleeve. In some embodiments, a proximal portion of a multi-channel sleeve may have a solid circumference. A region of solid circumference in a multi-channel sleeve may enhance stability of the multi-channel detachable member.

Instruments may access a bone fastener assembly through a passage in a sleeve. In some embodiments, a channel in a wall of a sleeve may extend a full length of the sleeve. In some embodiments, especially in embodiments of multi-channel sleeves, a channel in a wall of a sleeve may extend only a portion of the length of the sleeve. In some embodiments, a channel in a wall of a sleeve may extend 25%, 50%, 75%, 80%, 90%, 95% or more of the length of the sleeve. A channel can extend to a distal end of a sleeve such that a rod inserted in the channel may pass from the sleeve into a slot of a collar of a bone fastener assembly coupled to the sleeve.

A channel in a sleeve may be any of a variety of shapes. A channel may have a width that exceeds a width (e.g., a diameter) of the rod that is to be inserted in the channel. In some embodiments, a channel may be a linear opening parallel to a longitudinal axis of the sleeve. In some embodiments, a channel may have a non-linear shape including, but not limited to, a helical pattern, an arc, an "L" shape, or an "S" shape. A non-linear channel may allow a stabilization rod to travel along a predetermined path. In certain embodiments, adjacent sleeves may include channels with matching profiles, allowing ends of a stabilization rod to follow similar paths down the detachable member channels.

Coupling members may extend through portions of a sleeve to engage a collar to establish a radial orientation of the sleeve on the collar and/or to inhibit rotation of the collar relative to the sleeve. A distal end of a coupling member may be flat, curved, or angled. In some embodiments, a distal end of a coupling member may be threaded. In other embodiments, a distal end of a coupling member may be a projection that engages an opening in a collar. In some embodiments, an upper surface of a collar and/or a surface of a distal end of a coupling member may be textured to inhibit rotation of the collar relative to the sleeve. In certain embodiments, a proximal end of a coupling member may include a tool engaging portion. A tool engaging portion may include, but is not limited to, a hex section, a hexalobular section, a tapered section, a bead, a knot, a keyed opening, a coating, a threading, and/or a roughened surface for engaging a drive that rotates or otherwise displaces the coupling member.

Figure 2:
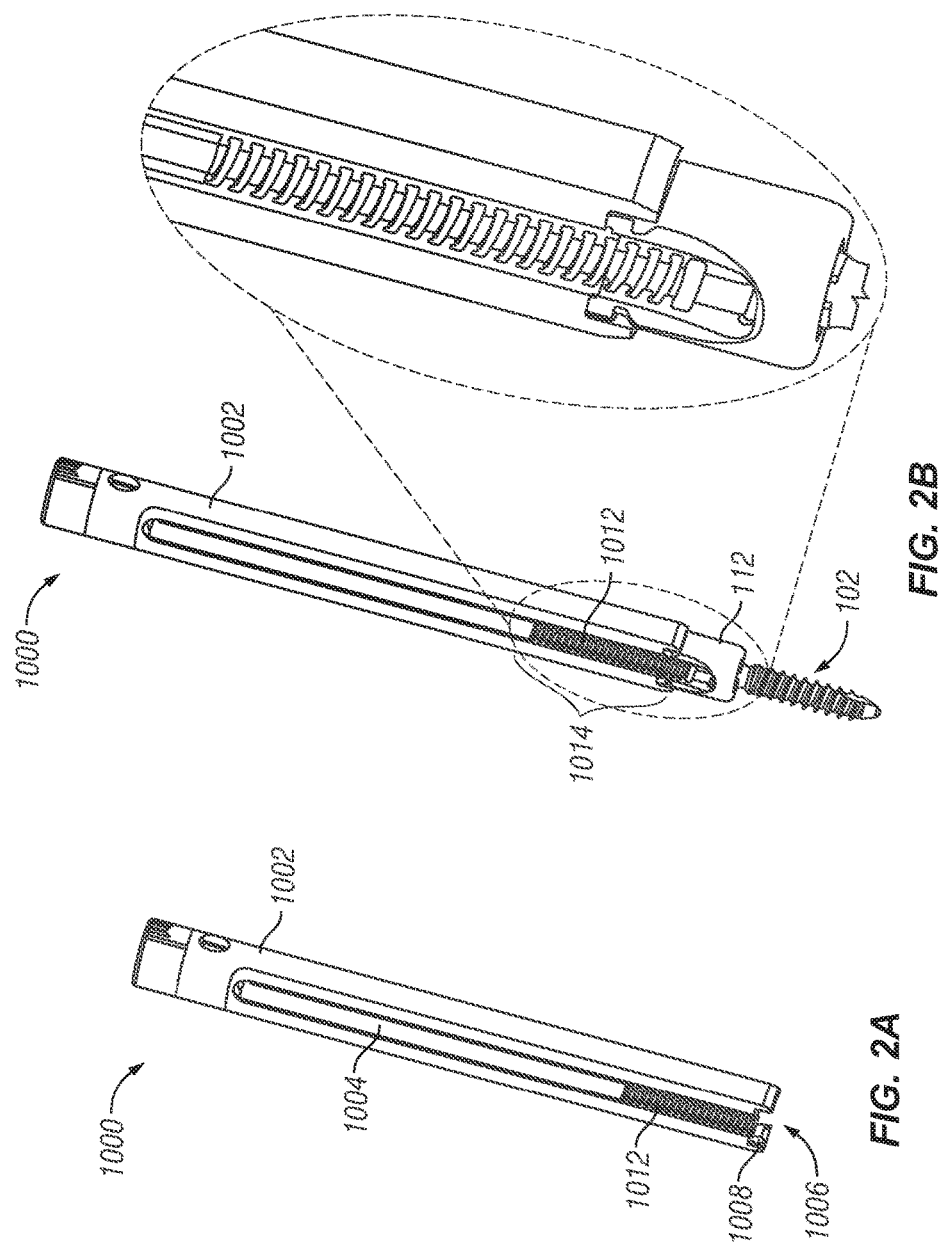
FIGS. 2A-2B depict an embodiment of a sleeve that can be used for reduction.

FIGS. 2A-2B are diagrammatic representations of a sleeve 1000 that can be used for reduction. Sleeve 1000 can be any single or multi-channel sleeve suitable for minimally invasive surgery that detachably connects to collar 112. Sleeve 1000 can include body 1002 defining one or more channels 1004 through the walls of body 1002 that are sized to fit a spinal stabilization rod 104. A passage 1006 from a proximal end to a distal end of body 1002 provides a workspace for various tools to reach collar 112 and allows a closure member to be engaged with collar 112. Body 1002 can include flange 1008 for coupling with a collar 112 and internal female threads 1012. Collar 112 can also include internal threads 148. When body 1000 is attached to collar 112, the threads of collar 112 and the internal threads 1012 of sleeve 1000 form a continuously threaded section that allows a closure member to be rotated down sleeve 1000 into collar 112. FIG. 2B illustrates sleeve 1000 connected to collar 112 and FIG. 2B illustrates that threads 1012 and threads 148 of collar 112 form a continuous set of threads 1014. While threads 1012 and threads 148 do not necessarily have to abut or contact each other when they form continuous set of threads 1014, they are selected so that continuous set of threads 1014 allows the closure member to transition from threads 1012 to threads 148. The threads 1012 or 148 can include any suitable standard threads or nonstandard threads such as modified threads described in U.S. patent application Ser. No. 11/779,406. According to one embodiment, threads 1012 and 148 can be selected so that the threads will not strip unless undue torque is used on a closure member. Threads 1012 and 148 have identical or different thread configurations (types, angles, sizes or other properties) as long as a closure member can safely transition from threads 1012 to 148 during a reduction procedure.

Threads 1012 can be disposed any length along sleeve 1000 including the entire length of sleeve 1000. In one embodiment, threads 1012 are at least long enough to allow a closure member to fully engage threads 1012 prior to contacting the stabilization rod for a desired level of reduction. For a 30 mm reduction, for example, threads 1012 can be disposed along at least 35-40 mm of body 1002.

In order for the closure member to be able to thread from body 1002 into collar 112, the threads 1012 and 148 can be timed. That is the angular orientation and position of the threads can be controlled to form a continuous set of threads down which a closure member can move. Even if the threads are properly timed, however, sleeve 1000, in some embodiments, can be attached to collar 112 in various orientations. One or more of the orientations may result in threads 1012 and 148 being misaligned such that the end of threads 1012 does not match up with the beginning of threads 148. To alleviate this problem, sleeve 1000 can include alignment features to ensure that the threads are properly oriented. For example, sleeve 1000 may include visible indicia for alignment or a coupling mechanism between sleeve 1000 and collar 112 that only allows sleeve 1000 and collar 112 to couple together with the threads properly aligned.

Figure 3:
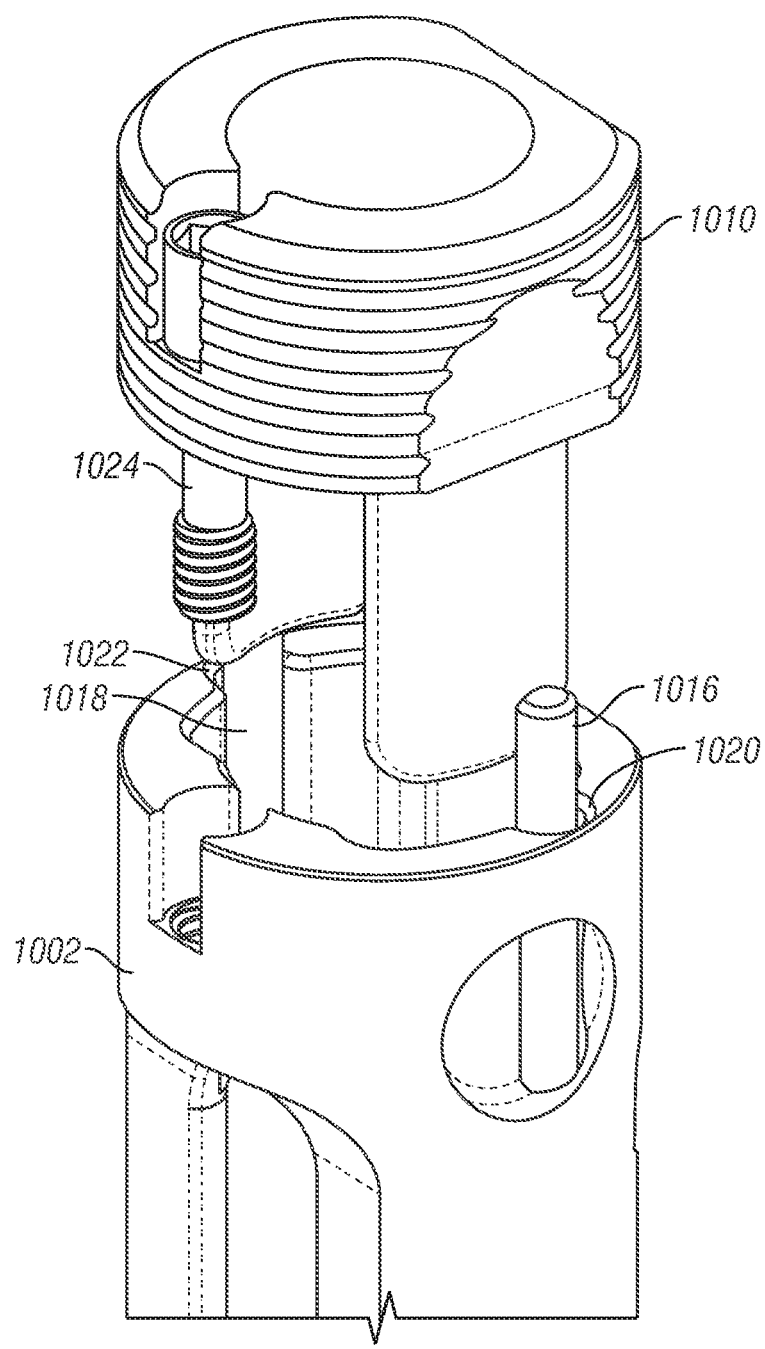
FIG. 3 depicts and embodiment of a quick release mechanism.

FIG. 3 is a diagrammatic representation of a coupling member that aligns sleeve 1000 and collar 112. In the embodiment of FIG. 3, head member 1010 connects to a body portion comprising two prongs 1016 and 1018. Prongs 1016 and 1018 can have different sizes, shapes, orientations or other characteristics so that the prongs 1016 and 1018 can only fit in corresponding recesses in collar 112 when sleeve threads 1012 are properly aligned with the threads of collar 112. Prongs 1016 and 1018 can be partially disposed in channels 1020 and 1022 along the walls of body 1002. In other embodiments, the channels for prongs 1016 and 1018 may form passages running internal to walls of body 1002. While only two prongs are shown, in other embodiments there can more than two prongs that are positioned to ensure proper alignment of the threads. A locking member 1024 can be used to securely couple head member 1010 to body 1002. In this example, locking member 1024 is a screw. However, in other embodiments, locking member 1020 can be a locking feature such as described for quick release mechanisms in U.S. patent application Ser. No. 11/779,406 that use a push motion, a twist motion, or a combination thereof or other locking mechanism as needed or desired. Additionally, the coupling member can be adapted to couple to collar 112 in one click as described, for example, in U.S. patent application Ser. No. 11/779,406.

Figure 4A:
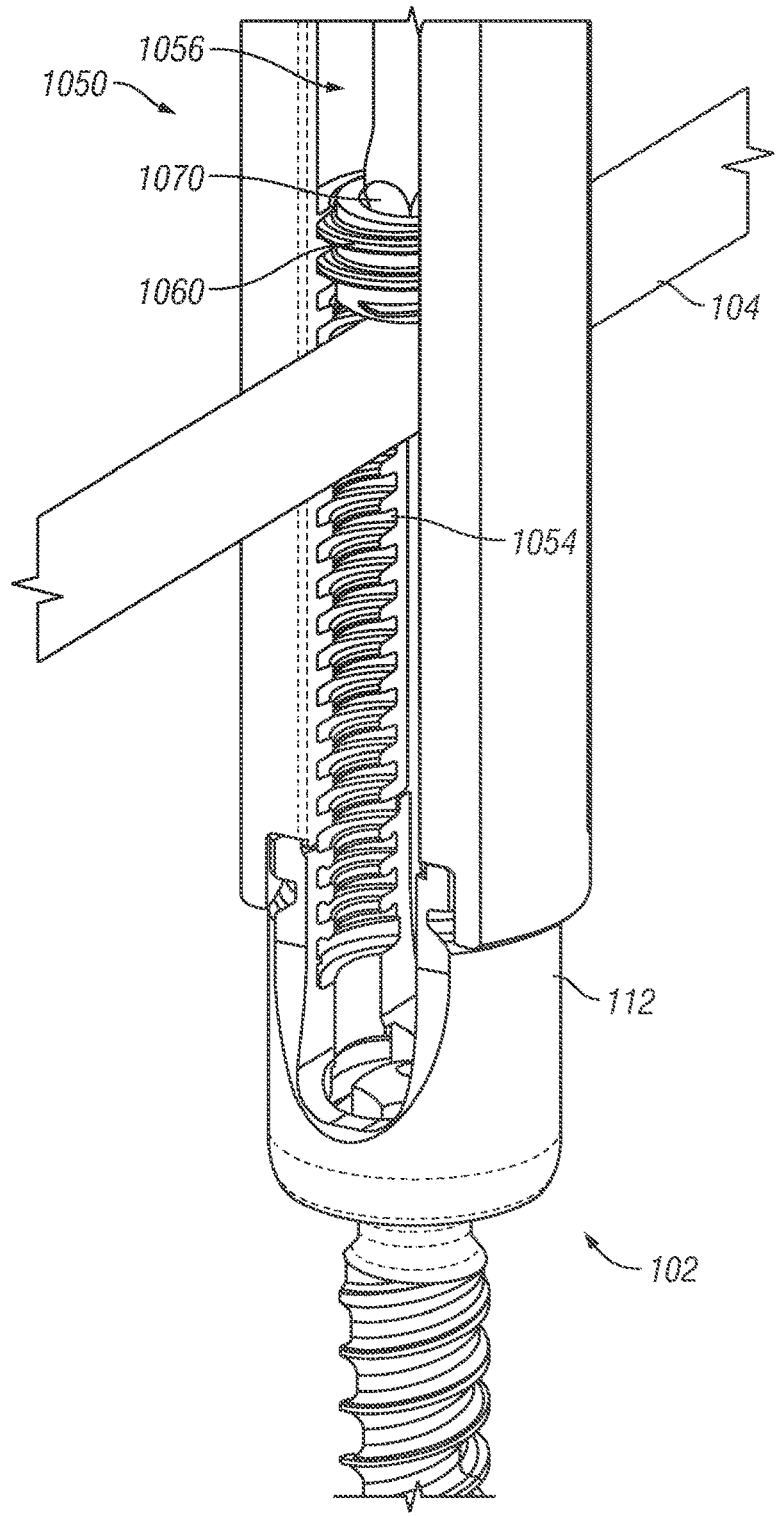
FIGS. 4A-4C are diagrammatic representations of performing reduction with a sleeve.
Figure 4B:
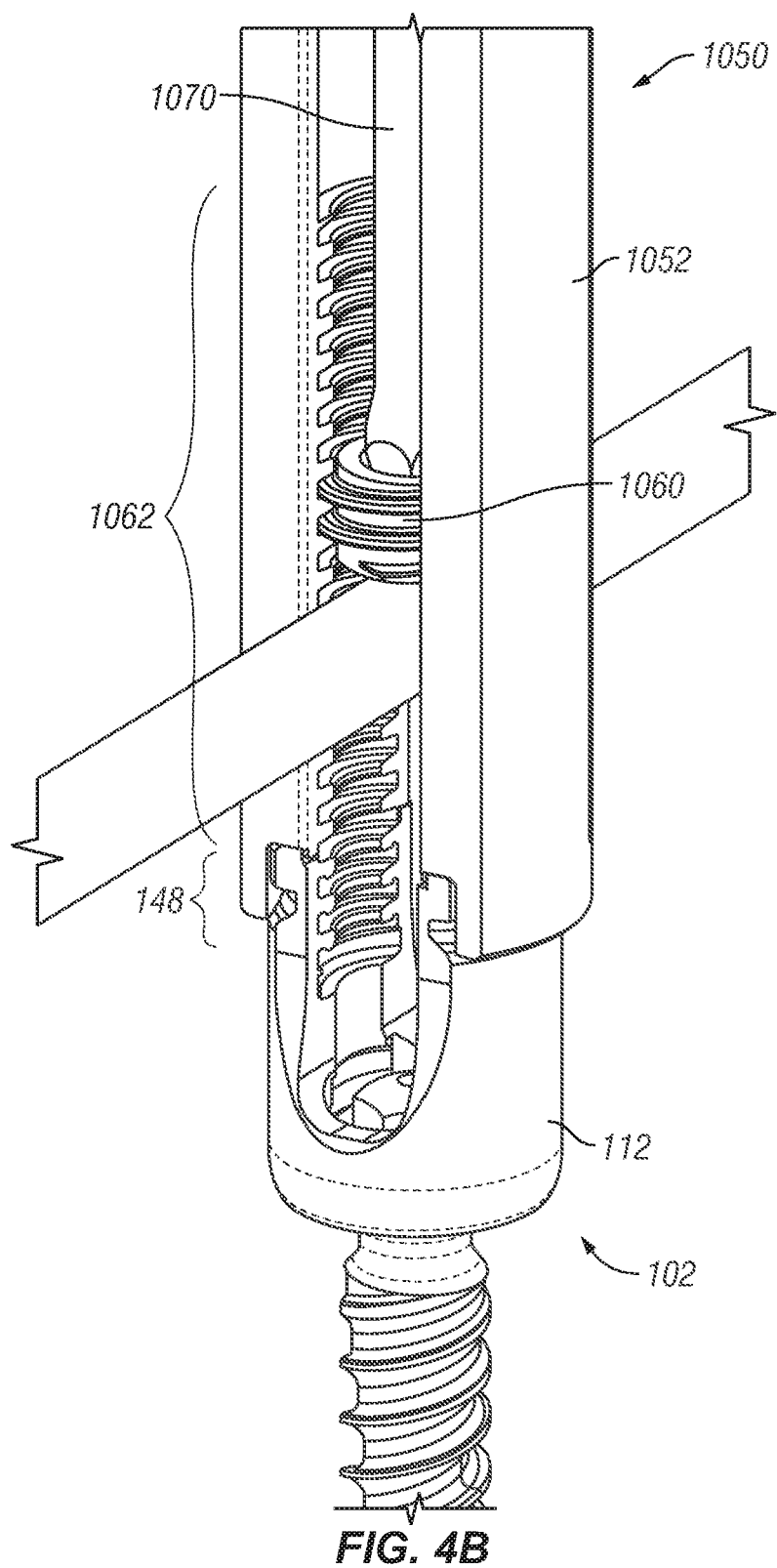
Figure 4C:
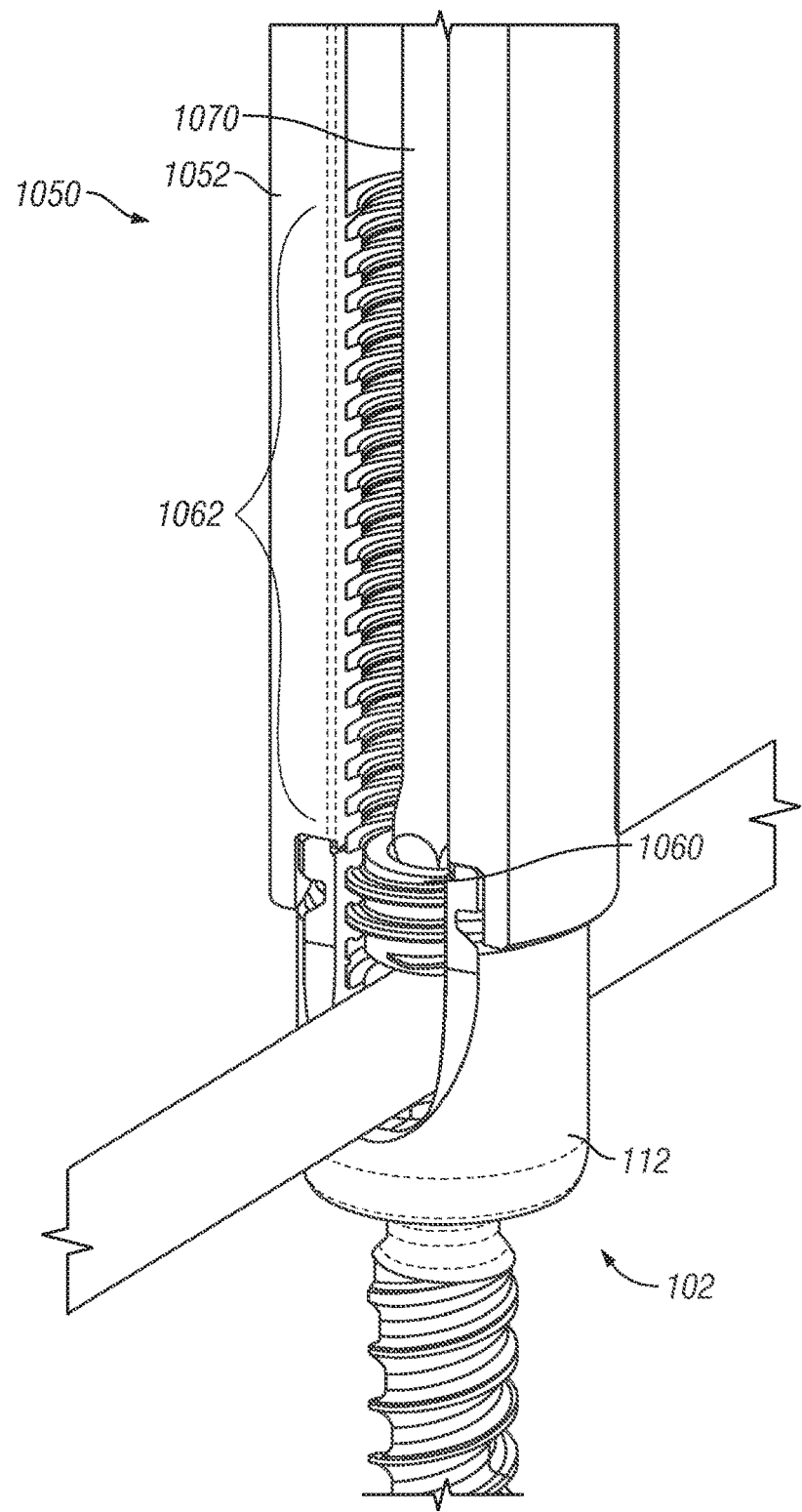

FIGS. 4A-4C are diagrammatic representations of an embodiment of reduction using a sleeve 1050. It can be noted in the example of FIGS. 4A-4C that sleeve 1050 is a multi-channel sleeve suitable for use in minimally invasive surgeries. However, reduction can also be performed using a single channel sleeve. Sleeve 1050 includes a body 1052 defining a passage 1054 and channels 1056. Threads 1062 are disposed along the walls of passage 1054. Sleeve 1050 is aligned so that threads 1062 form a continuous set of threads with threads 148 of collar 112. A tool 1070 can be used to turn closure member 1060.

Tool 1070 can include any suitable tool to turn closure member 1060 including, but not limited, hex, flat head, Philips head, star, socket or other type of driver known in the art. Tool 1070 can be a torque driver that will allow a user to apply up to a select amount of torque to closure member 1060. The maximum amount of torque can be selected to prevent the threads of closure member 1060 from stripping or, in the case of a shear off closure member, prevent a portion of closure member 106 from shearing. By way of example, but not limitation, tool 1070 can allow a maximum of 90 lbs/ft to be applied to closure member 1060. According to one embodiment, threads 1012 and 148 and the threads on closure member 1060 can be selected so that they will not strip based on a safety factor over the amount of torque allowed by tool 1070.

It is assumed for purposes of FIGS. 4A-4C that bone fastener assembly 102 is anchored to a vertebrae and rod 104 has been inserted into the body according to any suitable technique known or developed in the art. Sleeve 1050 can be selected to have threads 1062 that extend from collar 112 past rod 104 a distance sufficient to allow the threads of closure member 1060 to fully engage threads 1062 prior to contacting rod 104. This reduces the likelihood that the threads of closure member 106 will strip due to insufficient engagement with threads 1062 when closure member 106 asserts a force on rod 104.

A closure member 1060 can be placed in passage 1054 and engaged with threads 1062 using tool 1070. Closure member 1060 can be brought in contact with rod 104 and continually turned to force rod 104 into collar 112. If the torque required is greater than the amount set by tool 1070, a separate reduction device can be used to finish reduction. Reduction is complete when rod 104 is fully seated in collar 112. If a shear off closure member is used such as closure member 106 described above, tool 1070 can be reconfigured or another tool used to apply sufficient force to closure member 1060 to cause shear off.

Figure 5:
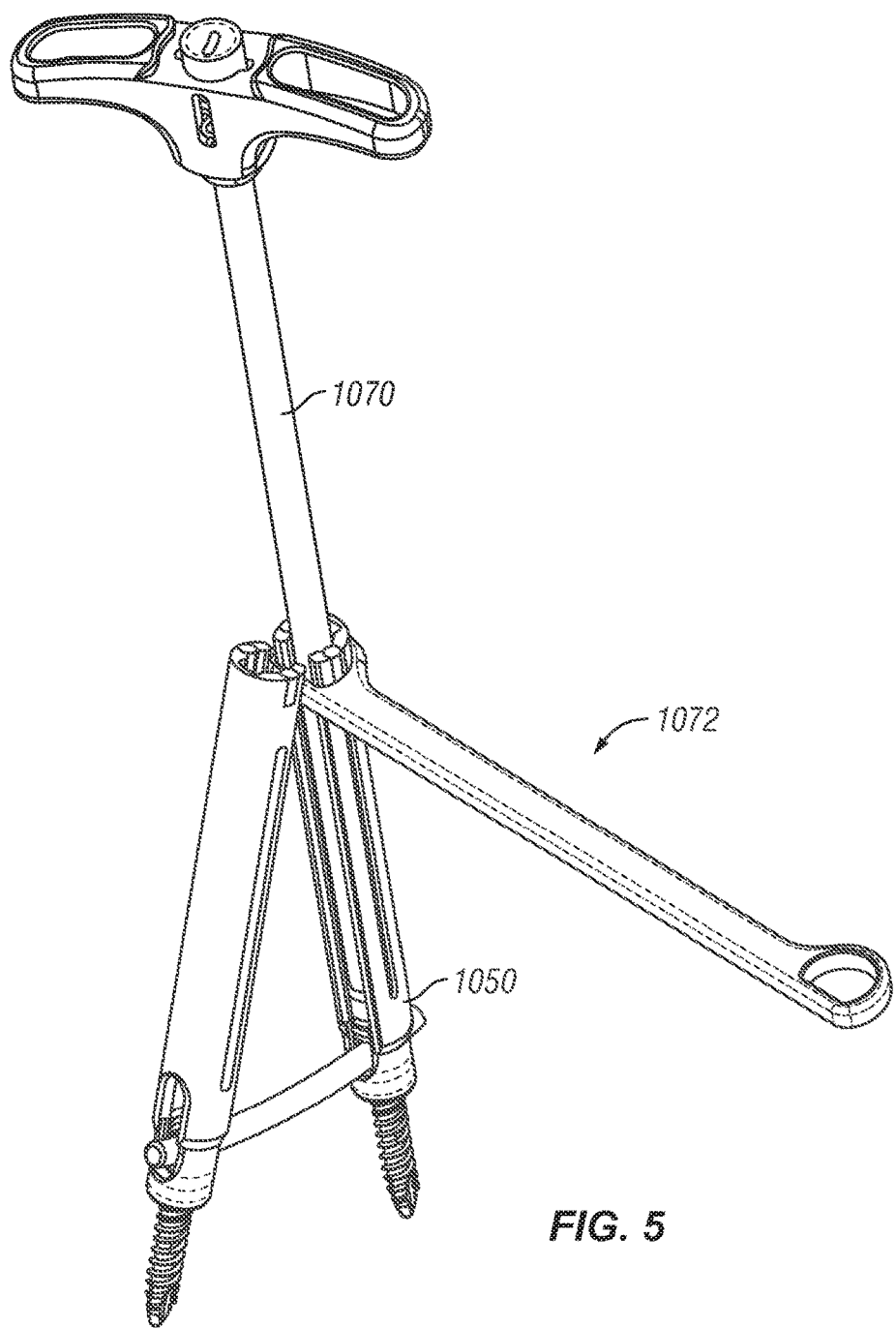
FIG. 5 is a diagrammatic representation of inhibiting rotation of a sleeve.

FIG. 5 illustrates one embodiment of inhibiting rotation of sleeve 1050. In the embodiment of FIG. 4l, tool 1070 is inserted in sleeve 1050 to turn closure member 106. A counter torque wrench 1072 can be used to prevent sleeve 1050 from rotating as force is applied to tool 1070. Counter torque wrench 1072 can be shaped to slip over sleeve 1050 on a portion of sleeve 1050 that extends outside of the patient's body. Force can be applied to counter torque wrench 1072 in a direction opposite to rotational force applied to tool 1070.

Embodiments described herein provide systems and methods to perform reduction using sleeves adapted for use in minimally invasive surgery. The sleeve can include internal threads that match those of a bone fastener assembly to provide a continuously threaded section. A closure member having complementary threads to the sleeve and collar can be screwed down the continuous set of threads move the rod into the collar. When the rod is fully seated in the collar the sleeve can be removed.

In the foregoing specification, the disclosure has been described with reference to specific embodiments. However, as one skilled in the art can appreciate, embodiments of the sleeves disclosed herein can be modified or otherwise implemented in many ways without departing from the spirit and scope of the disclosure. Accordingly, this description is to be construed as illustrative only and is for the purpose of teaching those skilled in the art the manner of making and using embodiments of a sleeve. It is to be understood that the forms of the disclosure herein shown and described are to be taken as exemplary embodiments. Equivalent elements or materials may be substituted for those illustrated and described herein. Moreover, certain features of the disclosure may be utilized independently of the use of other features, all as would be apparent to one skilled in the art after having the benefit of this description of the disclosure.

What is claimed is:

1. A reduction sleeve, comprising:
a sleeve body including an end adapted to be detachably coupled to a collar of a bone fastener assembly at a distal end of the sleeve body, the sleeve body defining:
a passage running from and an opening at the distal end to a proximal end, the passage sized to allow a closure member to travel from the proximal end to the distal end;
at least one channel through a wall of the sleeve body, the at least one channel sized to allow a portion of a spinal stabilization rod to move along the at least one channel, wherein the at least one channel extends to a slot in the collar, enabling the spinal stabilization rod to move from the at least one channel to the collar; and
a first set of threads disposed internal to the passage timed to and adapted to form a continuous set of threads with a corresponding second set of threads in the collar, wherein the continuous set of threads are adapted to engage external threads on the closure member; and
a coupling member including a cylindrical head member, two alignment prongs extending distally from the cylindrical head member and a locking member disposed through a portion of the cylindrical head member, the coupling member adapted to ensure that the sleeve body couples to the collar so that the first set of threads and second set of threads form the continuous set of threads to allow the closure member to transition from the first set of threads to the second set of threads;
wherein the reduction sleeve is adapted for use to perform reduction in minimally invasive surgeries to install a spinal stabilization system, and
wherein the locking member includes threads securely latching the coupling member onto the sleeve body.

2. The reduction sleeve of claim 1, wherein the locking member extends into the sleeve body to lock the coupling member onto the sleeve body;
wherein the sleeve body further comprises one or more additional channels running from the first end of the sleeve body to the second end of the sleeve body to accommodate the body portion of the coupling member;
wherein the body portion of the coupling member is configured to engage the collar of the bone fastener assembly through the sleeve to inhibit motion of the collar relative to the sleeve and the body portion is at least partially disposed in the one or more additional channels.

3. The reduction sleeve of claim 2, wherein the coupling member comprises asymmetrical prongs at least partially positionable in the one or more additional channels.

4. The reduction sleeve of claim 1, wherein the bone fastener assembly comprises a polyaxial bone screw.

5. A method of performing a minimally invasive spinal reduction procedure comprising:
  providing a bone screw coupled to a vertebrae, the bone screw comprising a collar having a first set of threads internal to the collar and defining a slot;
  coupling a sleeve, detachably, to the collar, the sleeve comprising:
  a sleeve body defining:
  at least one channel through a wall of the sleeve body sized to allow a portion of the spinal stabilization rod to move along the channel and into the collar of the bone screw;
  a passage extending from a first end of the sleeve to a second end of the sleeve sized to fit a closure member;
  a second set of threads internal to the passage timed to the first set of threads on the collar and positioned to form a continuous set of threads with the first set threads;
  inserting two alignment prongs of a coupling member through the sleeve to ensure that the second set of threads aligns with the first set of threads;
  securing a cylindrical head member of the coupling member to the sleeve using a locking member disposed through a portion of the cylindrical head member;
  inserting a portion of a spinal stabilization rod into the channel of the sleeve;
  inserting a closure member in the passage of the sleeve;
  mating threads on the closure member with the second set of threads before the closure member contacts the spinal stabilization rod; and
  turning the closure member with a tool to cause the closure member move the rod into the collar, wherein turning the closure member to cause the closure member to move the rod further comprises transitioning the closure member from the second set of threads to the first set of threads, and wherein the locking member includes threads securely latching the coupling member onto the sleeve body.

6. The method of claim 5, further comprising guiding the two alignment prongs of the coupling member into engagement with the collar of the bone screw to inhibit movement of first and second threads relative to each other and maintain the continuous threaded relationship.

7. The method of claim 6, wherein the sleeve further comprises one or more additional channels running from the first end of the sleeve body to the second end of the sleeve body and wherein the guiding the two alignment prongs further comprises guiding the two alignment prongs through the one or more additional channels to engage the collar and to prevent motion of the collar relative to the sleeve.

8. The method of claim 7, wherein the guiding the two alignment prongs includes guiding asymmetrical prongs.

9. The method of claim 8, further comprising locking the coupling member onto the sleeve using the locking member for latching onto the sleeve.

10. The method of claim 7, further comprising turning the closure member with a tool that limits the amount of torque that can be applied to the closure member.

11. A spinal implantation system, comprising:
  a spinal stabilization rod;
  a first bone fastener assembly and a second bone fastener assembly for fixing the spinal stabilization rod onto two or more vertebral bodies;
  a first sleeve comprising a first sleeve body having an end adapted to detachably coupled to a collar of a bone fastener assembly at a distal end, the first sleeve body defining:
  a passage running from and an opening at the distal end to a proximal end, the passage sized to allow a closure member to travel from the proximal end to the distal end;
  at least one channel through a wall of the first sleeve body, the at least one channel sized to allow a portion of the spinal stabilization rod to move along the at least one channel and adapted to meet a slot in the collar so that the spinal stabilization rod can move from the channel to the collar; and
  a first set of threads disposed internal to the passage timed to and adapted to form a continuous set of threads with a corresponding second set of threads in the collar of the first bone fastener assembly, wherein the continuous set of threads are adapted to engage external threads on the closure member;
  a coupling member including a cylindrical head member, two alignment prongs extending distally from the cylindrical head member and a locking member disposed through a portion of the cylindrical head member, the coupling member adapted to ensure that the first sleeve body couples to the collar of the first bone fastener assembly so that the first set of threads and second set of threads form the continuous set of threads; and
  a second sleeve adapted to detachably couple to the second bone fastener assembly;
  wherein the first sleeve and the second sleeve are adapted for use in a minimally invasive reduction procedure, and wherein the locking member includes threads securely latching the coupling member onto the first sleeve body of the first sleeve.

12. The spinal implantation system of claim 11, wherein the spinal stabilization rod is a rigid spinal stabilization rod.

13. The spinal implantation system of claim 11, wherein the spinal stabilization rod is a dynamic spinal stabilization rod.

14. The spinal implantation system of claim 11, further comprising a driver to screw the enclosure member along the continuous set of threads, wherein the driver is adapted to limit the amount of torque applied to the closure member.

* * * * *